Figure 1:
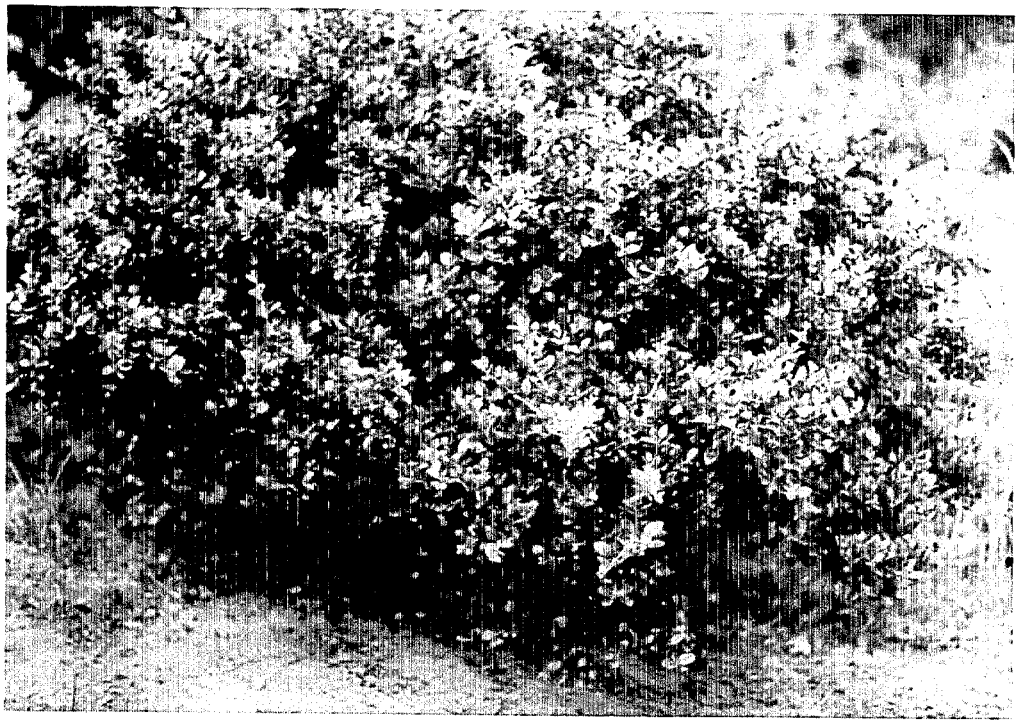

US00PP09543P

United States Patent [19]

Daniel, 3rd

[11] Patent Number: Plant 9,543

[45] Date of Patent: May 7, 1996

[54] *ILEX VOMITORIA —'BABY JEWEL' DWARF YAUPON*

[76] Inventor: Theo S. Daniel, 3rd, 4022 County Rd. 4709, Athens, Tex. 75751

[21] Appl. No.: 365,221

[22] Filed: Dec. 28, 1994

[51] Int. Cl.[6] ..... A01H 5/00

[52] U.S. Cl. ..... Plt./65

[58] Field of Search ..... Plt./65

[56] References Cited

U.S. PATENT DOCUMENTS

P.P. 8,779 6/1994 Pittman ..... Plt./65

*Primary Examiner*—James R. Feyrer

[57] ABSTRACT

A new and distinct yaupon holly plant (*Ilex vomitoria*) which is particularly distinguished by being of female gender, being dwarf, and having tolerances of high and low temperatures uncommon within the species. This plant matures into mounded specimens of high density due to its lack of terminal dominance and high level of natural branching with each growth flush. This plant is unusually easy to root from cuttings and begins forming a heavy crop of attractive red berries on market liners of small size, allowing the mature characteristics of the plant to be seen at a stage where the plant could be marketed as small specimens in retail outlets, a distinct advantage for plants of this market class.

1 Drawing Sheet

The present invention relates to a new and distinct plant seedling of yaupon holly (*Ilex vomotiria*) in the Aquifoliaceae family.

This new highly unique seedling hereafter referred to as 'Baby Jewel' Dwarf Yaupon appears to be a seedling produced naturally and by accident as a result of cross pollination among *Ilex vomitoria* specimens in a large field of nursery-grown plants. I originally discovered the mother plant in late 1939 at Henderson's Nursery (later renamed Daniel Landscape Nursery), approximately two miles southeast of the Courthouse Square in Athens, Henderson County, State of Texas, near U.S. Highway 175, in a field of *Ilex vomotoria* probably planted around 1935 from seedling liners from an known source. Many of the tree-type plants were sold, but all of the dwarfs were left in the field. After I bought the nursery, I continued selling tree types from that block until in 1958 there were 4,012 hollies left there. I guarded the dwarfs, put stakes around them, indicating that they were not for sale, then later moved all the original dwarfs and several tree types to my lawn a few hundred yards east of the block—where they remain.

This new Ilex seedling, 'Baby Jewel' dwarf yaupon, appeared quite different form most yaupons in the block. After careful observation of its many extraordinary features over a period of years, I decided that it was superior to the other dwarfs growing near it and embarked on an ambitious project to experimentation and propagation. In an experimental block of several thousand plants grown from its seed, only two or three resembled it, and they were not as dwarf-growing or produced as heavy a berry crop as the parent. A few plants were male dwarfs. All other seedlings grew into semi-dwarf trees. My work with it has been kept secret until now.

This new seedling has been reproduced numerous times by asexual propagation (vegetative cuttings). Each of the progeny exhibited identical characteristics of the original selection indicating extremely stable genes, and establishing this seedling as reproducible and true to type. 'Baby Jewel' specimens planted in the ground are hardy in all extremes of weather or soil conditions in this area. But in the 1980's, an unheard-of 15 degrees below zero struck my nursery, killed 300 year-old post oak trees, all the 'Stokes', 'Devirecta' and 'Schillings' varieties of dwarf Yaupons I was growing as controls to evaluate 'Baby Jewel', and killed several hundred thousand 'Baby Jewel' specimens in one-gallon and five-gallon containers sitting on sheets of black plastic in an open area exposed to strong north winds. I started over and now have over 12,000 in five-gallons, and several thousand in two-inch pots. They will soon be shifted to larger containers. My primary source of cuttings is from plants growing in my fields which were grown from cuttings of the original 'Baby Jewel' plant.

'Baby Jewel' has many desirable and highly distinctive characteristics which render it absolutely unique from any other dwarf *Ilex vomitoria* presently offered in the nursery trade. For example, all other known dwarf yaupons have narrow (linear) leaves; whereas this plant has rounded leaves. Those other varieties have slender twigs with leaves farther apart on the stems than mine. The new twigs or stems on mine are stubby and thicker, and due to short internodes leaves whorl closely on the stems, giving a compact, attractive, uncommonly dense appearance to the plants. Whereas all other varieties have lighter green color, 'Baby Jewel' has a darker-green color. Dr. Fred C. Galle, of the Ida Callaway Cason Gardens in Georgia, and all other recognized authorities on Ilix, say that all dwarf yaupons are staminate (males). The truly remarkable characteristic of Baby Jewel is that it is pistillate (female)! Not only that, but the bright-red berries often whorl in clusters so tightly that they form red ropes!

Due to the exceptional combination of desirable characteristics of dwarfness, habit, hardiness, plant coloration and tolerances of extremes expressed by this plant, it is believed that it will constitute a valuable and unique addition to the market class of plants available having similar utility in landscape appointment, hedge formation, ground cover uses and garden decoration. Additionally being female, this plant produces attractive fruit, which adds color splashes where it is planted, as well as providing food for wildlife when other sources are exhausted. The slow growth rate of this plant, combined with its dense growth habit, makes it ideal for pruning into minature topiary forms—especially when grown in containers. Its denseness is indicated by the length of its internodes: from three-sixteenths to five-sixteenths inches.

This plant is immune to nemotodes, crown gall, cotton root rot, leafspot, and powdery mildew.

BRIEF DESCRIPTION OF THE PHOTOGRAPHS

FIG. 1 shows a thirty-six-year-old 'Baby Jewel' plant cutting grown from the original 'Baby Jewel' plant. Photograph was taken Jun. 14, 1994. This unsheared plant was growing in a red clay field, and was uncultivated, unfertilized, and nonirrigated.

Figure 2:
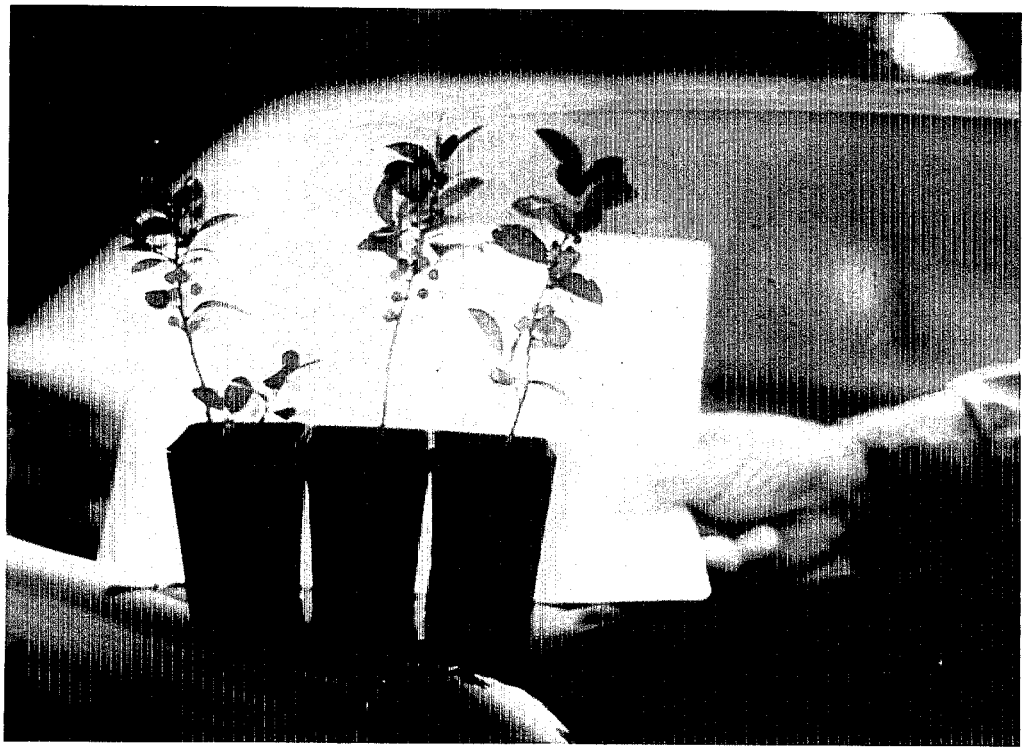

FIG. 2 shows three-year-old 'Baby Jewel' rooted cuttings growing in two-inch pots in a greenhouse. Photograph was taken Jun. 14, 1995. Note last year crop of red berries, and current season crop of green berries.

DETAILED PLANT DESCRIPTION

The following is a detailed description of the performance and appearance of the *Ilex vomitoria* seedling, Baby Jewel Dwarf Yaupon. Descriptions are based on 186 plants growing in my nursery fields. Color determinations and comparisons are based on Maerz and Paul's *A DICTIONARY OF COLOR,* first Edition 1930.

Overall size and growth habit:

*Size.*—The subject 186 plants were rooted in greenhouse beds from cuttings taken on Apr. 28, 1958 from the original selection. After eighteen months, they were shifted to two-inch pots and put in lath (shade) houses. They were successively shifted to larger and larger pots. On Jan. 6, 1967 they were planted in my "Test Block" by me and two helpers. Today, at the age of 36 years, they average 4 to 4½ feet in height and 4½ to 5½ feet in width.

*Habit.*—Rounded, compact, and dense. The many, many branches are hidden from view by the dense foliage.

Foliage:

*Size.*—Length (from petiole to leaf apex) — 1¼ to 1⅝ inches. Width — ¾ to ⅞ inches. Margins — Sinuate (entire). (FIG. 2). Shape — oval. Apex — obtuse. Base — rounded. Petioles — ⅛ to 3/16 inches.

*Color.*—Winter color — upper leaf surface of mature leaves: Plate 31, E 8. Lower leaf surface of mature leaves: Plate 29, B 6. Summer color — same as Winter color.

Stem color:

*Winter color.*—Newly emerging and young undeveloped stems: Plate 7, L 6. Mature stem (one to two years growth): Plate 7, A 3.

*Summer color.*—Same as Winter color.

Inflorescence and fruit:

*Flowers.*—Pistillate, in terminal clusters borne on the preceding season's growth. Four petals.

*Size.*—Fully open blooms are 5/16 to 7/16 inches in diameter.

*Fruit.*—Globose. ¼ to 5/16 inch in diameter; formed in abundant quantities.

*Fruit color.*—Plate 1, L 6. Attachment of full color dependent on dates of freezing weather — normally December in East Texas.

Environmental tolerances:

*Heat tolerance.*— Baby Jewel Dwarf Yaupon showed no sign of stress sixty miles southeast of Dallas, Tex. in parched, nor-irrigated fields in full sun during temperatures of 110 degrees F., and low humidity.

*Hardiness.*— Baby Jewel planted in the ground sustained no damage in an "unheard-of" 15 degrees below zero F blast which killed 300 year-old post oak trees in the same area.

REFERENCES

Bailey, L. H., 1930 THE STANDARD CYCLOPEDIA OF HORTICULTURE, McMillan, New York.

Texas Forest Service, Bulletin 20, FOREST TREES OF TEXAS, page 97, College Station, Tex.

I claim:

1. A new and distinctly different variety of *Ilex vomitoria* plant substantially as shown and described, characterized by:

a. having oval leaves with a length generally in the range of 1¼ to 1⅝ inches long and ¾ to ⅞ inches wide, with sinuate or wavy margins, b. a globose fruit ¼ to 5/16 inches in diameter produced in abundant quantities, and c. a tolerance of temperatures which have raged from 110 degrees F. to minus 15 degrees F.

* * * * *